United States Patent [19]

Helman et al.

[11] Patent Number: 5,164,406

[45] Date of Patent: Nov. 17, 1992

[54] METHOD FOR ENHANCING TRANSDERMAL PENETRATION AND COMPOSITIONS USEFUL THEREIN

[75] Inventors: Michael D. Helman, Edison; Alison B. Lukacsko, Robbinsville; Thomas A. Re, Hazlet, all of N.J.; F. Christopher Zusi, Tonawanda, N.Y.

[73] Assignee: Bristol-Myers Squibb Co., New York, N.Y.

[21] Appl. No.: 353,890

[22] Filed: May 22, 1989

Related U.S. Application Data

[63] Continuation-in-part of Ser. No. 201,659, Jun. 2, 1988, abandoned.

[51] Int. Cl.$^5$ .................... A61K 31/40; A61K 31/44
[52] U.S. Cl. .................... 514/357; 514/396; 514/397; 514/651; 514/938; 514/946; 514/947
[58] Field of Search ............... 514/946, 947, 396, 357, 514/397, 651, 938

[56] References Cited

U.S. PATENT DOCUMENTS

| | | | |
|---|---|---|---|
| 4,732,892 | 3/1988 | Sarpotdar et al. | 514/178 |
| 4,879,275 | 11/1989 | Minaskanian | 514/946 |
| 4,908,389 | 3/1990 | Mahjour et al. | 514/946 |

FOREIGN PATENT DOCUMENTS

| | | | |
|---|---|---|---|
| 0164520 | 9/1983 | Japan | 514/947 |
| 1020508 | 2/1966 | United Kingdom | 514/844 |
| 1026778 | 4/1966 | United Kingdom | 424/73 |
| 1321024 | 6/1973 | United Kingdom | 560/80 |

OTHER PUBLICATIONS

Iwata et al., "Adriamycin Ointment with Addition of Napholine Nitrate . . . ", *Yakuzaigaku*, 48, (1), (1988), pp. 64-69, Chem. Abs., Sep. 5, 1988, vol. 109, No. 10, 79612b.

*Primary Examiner*—Dale R. Ore
*Attorney, Agent, or Firm*—Sandra M. Nolan

[57] ABSTRACT

The present invention provides for a composition containing a pharmacologically active agent and a selected imidazole or an imidazole derivative, such composition exhibiting enhanced penetration of the pharmacologically active agent component when a composition containing the aforementioned components is applied to skin.

A method of enhancing dermal penetration of compositions containing a pharmacologically active agent is also provided.

19 Claims, No Drawings

METHOD FOR ENHANCING TRANSDERMAL PENETRATION AND COMPOSITIONS USEFUL THEREIN

This application is a continuation-in-part of co-pending application Ser. No. 201,659, filed Jun. 2, 1988, now abandoned.

FIELD OF THE INVENTION

This invention relates to the enhancement of transdermal penetration of various topically applied preparations. More specifically this invention concerns the use of imidazole or imidazole derivatives to enhance transdermal penetration of a pharmacologically active agent through the skin and into the systemic circulation, particularly in applications where a preparation containing these ingredients is applied to human skin.

BACKGROUND OF THE INVENTION

Topical application of therapeutic agents has received and is presently receiving considerable attention. Notwithstanding, applicants are unaware of any teaching or suggestion in the prior art that imidazole or imidazole derivatives can be utilized in conjunction with a pharmacologically active agent to affect improved transdermal penetration of such agent.

U.S. Pat. No. 4,627,131 which issued Jun. 30, 1987 to Higuchi et al., teaches certain novel cyclic ureas, i.e. 2-imidazolidinone and 4-imidazolin-2-one derivatives, as being useful for enhancing drug absorption through the skin. The compounds taught by Higuchi et al. are structurally dissimilar from the compounds of the present invention, as will be noted from the following comparative structural formulae:

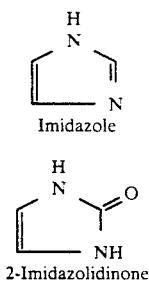

Imidazole  I

2-Imidazolidinone  II

The 2-imidazolidones are cyclic ureas. These compounds have a double bonded oxygen at the 2-position. This places the compounds in a different chemical class from imidazole and its derivatives.

The compounds of structures I and II are in some respects similar. Both are polar molecules of low to intermediate molecular weight. Both have high-boiling points and are compatible with polar and non-polar solvents. Neither has a definite absorption maximum in the near ultraviolet range. Both are based upon the imidazole ring, i.e. a five-membered ring containing two nitrogen atoms separated by one carbon.

Notwithstanding, the carbonyl function at the 2-position of the compound of the structure II profoundly alters the physiochemical properties of the molecule. The carbonyl function eliminates the basic properties of imidazole (I). This has important physiological ramifications. Imidazole and imidazole derivatives in accordance with the present invention generally have pKa's (acid dissociation constants) in the range of 6 to 8, depending on their substitution. This means that in physiological systems (pH near 7.0), they are appreciably charged (partially protonated). This affects their interaction with highly non-polar media such as the interior of cell membranes, and with charged species, such as membrane surfaces, amino acids and physiological ions. In contrast, the compounds of structure II have no corresponding basic properties and they are uncharged in physiological media.

The carbonyl group also affects the chemical properties of the ring. By donating electrons, it changes the reactivity of the compound to certain reagents. Imidazole and imidazole derivatives in accordance with the present invention do not undergo Friedel-Crafts acylation without decomposition. In contradistinction thereto, compounds of structure II are readily acylated under standard conditions. The oxygen atom also causes greater localization of the double bonds in compounds of structure II, rendering them more susceptible to chemical reduction. Imidazoles and imidazole derivatives in accordance with the present invention remain unaffected even by drastic reducing conditions. This indicates a change in the aromaticity of the ring.

The oxygenation of compounds of structure II also changes the properties of 1,3-disubstituted derivatives (Ia compared to IIa; side-chain shown as methyl for comparison):

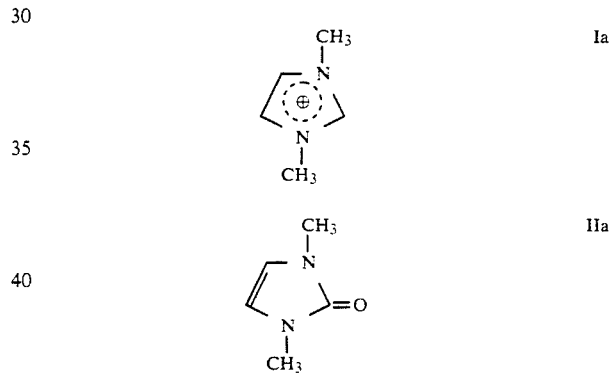

Compound Ia is a quarternary ammonium salt. It is a charged molecule whose charge is not susceptible to change by manipulating the pH of its solution. It is also unstable to heat—it will eliminate one of the methyl groups (attached to the counter-ion—not shown) and revert to 1-methylimidazole. In contrast thereto, compound IIa is not charged and is heat stable.

The change in the charge behavior is the quality most strongly differentiating the imidazole and imidazole derivatives and the compounds of formula II. Charged species will attract counter-ions and repel ions of the same charge. They tend to be expelled from non-polar media and to be concentrated in aqueous media. Uncharged species do the reverse. Since we do not understand the mechanism of skin penetration enhancement, it is not possible to predict which combination of properties is most desirable. However, it should be obvious that since the properties of the imidazole and imidazole derivatives in accordance with the presence invention and the compounds of formula I and II are very different, the penetration—enhancing activity of one would not be predictive of the activity of the other.

SUMMARY OF THE INVENTION

The present invention is directed to the enhancement of transdermal penetration of various topically applied pharmacologically active compounds, and, in particular relates to compositions having improved transdermal penetration comprising imidazole or an imidazole derivative in combination with a pharmacologically active agent.

Generally such compositions will also contain other ingredients such as carriers, emollients and the like which are conventionally found as components of topically applied preparations.

As used herein "enhancement of transdermal penetration" means an increase in the amount of pharmacologically active agent which traverses the skin and is taken up systemically.

DETAILED DESCRIPTION OF THE INVENTION

It has been found that the transdermal penetration of a given pharmacologically active compound can be substantially improved by incorporating into a composition containing said pharamacologically active compound a transdermal penetration enhancing amount of imidazole or an imidazole derivative.

This unexpected effect is quite useful in that it allows one to improve the transdermal delivery of the pharmacologically active compound from the composition, thereby allowing one to achieve the same level of efficacy with a lower overall concentration of the pharmacologically active compound in the composition.

The improved transdermal penetration effect which is the subject of the present invention is evident with various pharmacologically active agents (including, but not limited to, antihistamines, such as for example tripelennamine, triprolidine, diphenhydramine and, chlorpheniramine) all of which may be employed either as the free base or as a pharmaceutically acceptable salt, in combination with a transdermal penetration enhancing amount of imidazole or an imidazole derivative (including, but not necessarily limited to, xylometazoline HCl, naphazoline HCl, oxymetazoline HCl, miconazole, econazole and clotrimazole).

In addition to antihistamines, other pharmacologically active agents may also have their skin penetration enhanced by the method of the present invention. Such agents include but are not limited to, the following:

Anti-bacterials; deodorants; anti-ulcer, antispasmodic and other drugs effecting the gastrointestinal tract; NSAIDS (such as for example aspirin and ibuprofen); analgesics (such as for example aspirin and ibuprofen); antipyretics, anti-inflammatories (such as for example aspirin and ibuprofen); steroids; (such as for example prednisone, prednisolone and hydrocortisone and pharmaceutically acceptable salts thereof) antifungal agents; antihypertensive agents; sympathomimetic amines (such as for example xylometazoline, phenylephrine, naphazoline and metaproterenol); central nervous system active agents; diuretics (such as for example hydrochlorothiazide); antitussives (such as for example dextromethorphan); vasodilators (such as for example nitroglycerin); anti-nauseants; and compounds for treating motion sickness.

Certain of the imidazole and imidazole derivatives disclosed herein as enhancing the transdermal penetration of pharmacologically active agents can penetrate to an extent sufficient to exert their own pharmacological effect. Xylometazoline and naphazoline are prime examples of this.

Normally, the pharmacologically active agent and the imidazole or imidazole derivative will be present in an aqueous vehicle containing an emollient and a surfactant in amounts which will be dictates by dosage considerations and the conditions of intended use, all of which are within the ability of one skilled in the art to determine and therefore will not be described in further detail here.

In the preferred embodiment the compositions will preferentially contain up to about 5.0 wt. % of pharmacologically active agent and from about 0.5 wt. % up to about 5.0 wt. % of imidazole or imidazole derivative, based upon the total weight of the prepared composition.

More preferably, from about 0.05 wt. % to about 3.0 wt. % imidazole or imidazole derivative will be present and most preferably from about 0.25 wt. % to about 1.0 wt. % will be used. Typically 0.5 wt. % of imidazole or imidazole derivative will be adequate to achieve enhanced penetration.

The imidazole or imidazole derivatives useful in the present invention are those selected from the group defined by the following:

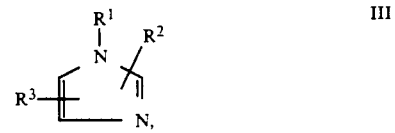

III wherein $R^1$, $R^2$ and $R^3$ are independently selected from the group consisting of hydrogen, halogen, nitro, carboxylic acid hydrazide, alkyl of from 1 to 20 carbon atoms, alkoxy of from 1 to 20 carbon atoms, aryl, $C_1-C_5$ alkyl substituted by alkenyl of from 2 to 20 carbon atoms, amino $C_1-C_5$ alkyl, acyl of from 2 to 20 carbon atoms and

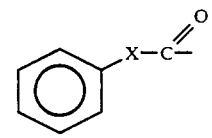

wherein X is $-CH_2=CH-$ or alkylene of from 1 to 5 carbon atoms, provided that $R^2$ may also be $SR^4$ wherein $R^4$ is hydrogen or lower alkyl, and, further provided, that at least one of $R^1$, $R^2$ and $R^3$ is hydrogen; and pharmaceutically acceptable salts thereof;

(b) an imidazole derivative selected from the group consisting of naphazoline, xylometazoline and oxymetazoline; and pharmaceutically acceptable salts thereof; and (c) mixtures thereof.

Preferred compounds of Formula III are imidazole, 1,2-dimethylimidazole, 1-dodecylimidazole, 4-methyl imidazole, 1-decyl imidazole, methimazole, 4-hydroxymethyl imidazole, 1-methyl imidazole, 4-phenyl imidazole, 2-isopropyl imidazole, D-histidine, 1-cyanoethyl-2-phenylimidazole, 1-(3,7-dimethyl-2,6-octadienyl) imidazole, 2-methyl imidazole, N-propionyl imidazole, N-(3-aminopropyl)imidazole, 2-propyl imidazole, 4-carboxylic acid ester of imidazole, 1-butyl imidazole, and pharmaceutically acceptable salts thereof.

More preferred compounds of Formula III are imidazole, 1,2-dimethyl imidazole, 1-dodecyl imidazole, 4-methyl imidazole, 1-decyl imidazole, methimazole, 4-hydroxymethyl imidazole, 1-methyl imidazole, 4-phenyl imidazole, 2-isopropyl imidazole, and pharmaceutically acceptable salts thereof.

Most preferred compounds of Formula III are imidazole, 1,2-dimethyl imidazole, 1-dodecyl imidazole, 4-methyl imidazole, 1-decyl imidazole, and pharmaceutically acceptable salts thereof.

In vitro transdermal penetration studies have demonstrated that, surprisingly, the presence of a selected imidazole or imidazole derivative compound of the present invention can enhance the transdermal penetration of, for example, an antihistamine compound, as much as eleven-fold.

In vivo studies in human subjects have demonstrated that imidazole and imidazole derivatives in accordance with the present invention can increase the vasoconstrictive activity, hence transdermal penetration, of steroids.

While the invention has generally been described above, the details of the present invention will be better understood by recourse to the examples which follow.

GENERAL TEST PROCEDURE

Unless otherwise indicated in all of the following examples the pharmacologically active compound and imidazole or imidazole derivative were formulated in a typical oil/water emulsion base, identified as B in the following tables and comprising:
Polyoxyethylene stearyl ethers, 3 wt. %
Polyoxypropylene fatty alcohol ethers, 3 wt. %
Deionized water, 94 wt. %

Further, in all cases, unless otherwise noted, the tests were carried out at 37° C. and results were compared to penetration data for the same material in the oil/water emulsion base. Moreover, all percentages of composition components recited are, unless otherwise indicated, weight percent (wt. %) and are based upon the the total weight of the composition.

Rat Skin (in vitro)

The test method is carried out as follows:

A. Prior to testing, rats are routinely acclimated to the laboratory environment for seven days and gross observations are made to ensure good health of the animals to be tested.

B. Female Sprague Dawley rats (190-240 gm) are selected for testing and identified by cage label and ear tag number.

C. Diffusion Cell Preparation.

1. An O-ring is placed on a standard Franz Diffusion Cell. A stir bar is placed in the receptor compartment. Each cell is filled with approximately 4.5 ml sterile physiologic saline (receptor compartments are calibrated to contain 5.0 ml).

2. The jacketed diffusion cells are maintained at 37° C.±1° (or alternatively desired temperature) using an external water bath and a circulating pump.

D. Skin Section Preparation and Mounting

1. Test animals are sacrificed by intraperitoneal injection of 0.4 ml/100 gm. body weight sodium pentobarital (1 gm/ml).

2. The backs are lightly shaved using electric hair clippers.

3. A section of skin, measuring approximately 8 cm long by 7 cm wide, is removed from the back of each rat using a No. 20 scalpel assuring that the skin section is free from subcutaneous fat.

4. A piece of the skin section is mounted over an O-ring on the diffusion cell, epidermal side facing up. The donor compartment is placed on top of the skin section making a complete seal over the skin. A clamp is used to secure the skin section in place.

5. Air bubbles that collect under the skin are removed by inverting the diffusion cell and tapping it gently. The receptor compartment is filled with sterile physiologic saline to 5.0 ml.

E. Application of Test Materials

1. Test and control materials are applied to the skin using s syringe or spatula. The material is spread evenly and completely over the exposed skin surface using the tip of the syringe/spatula.

F. Sampling Procedure

1. An HPLC carousel is loaded with microvials. Springs and inserts are placed into the microvials.

2. Receptor compartments are sampled at desired time intervals using a microliter ($\mu l$) syringe. The sample (approximately 160 $\mu l$) is placed into the insert. The microvial is sealed with a plastic cap.

3. When multiple sampling is required, the receptor compartment is replenished with sterile physiologic saline to maintain a 5.0 ml volume.

G. Analysis

Samples are analyzed using standard analytical techniques. The presence of test material in the samples is indicative of transdermal penetration.

Human Skin (in vitro)

The test procedure is as described for rat skin studies with the exception that normal excised human skin samples obtained from breast reduction surgery are utilized.

Pig Skin (in vitro)

The test procedure is as described for rat skin studies with the exception that excised pig skin samples from Yucatan miniature pigs are utilized.

EXAMPLE I

In order to determine the capability of imidazole and imidazole derivatives to enhance dermal penetration of the antihistamine tripelennamine HCL (TPL), formulations containing 2% TPL in an emulsion base (B) were prepared and tested as described above. Imidazole or an imidazole derivative was incorporated therein and the resultant composition was tested as described above. The results of determinations for a series of test evaluations made are presented in the following Tables 1 and 2. As evident from the data of Table 1, with levels of addition of imidazole of up to 1.0%, tripelennamine HCL (TPL) penetration increased approximately 340% as compared to the control. The data of Table 1 further indicates that transdermal penetration is a function of the concentration of imidazole employed.

TABLE 1

2% TRIPELENNAMINE HCL IN OIL/WATER EMULSION BASE (RAT SKIN)

| COMPOSITION | 24 HOUR PENETRATION (TOTAL MICROGRAMS BASE*) | INCREASE IN PENETRATION RELATIVE TO CONTROL** |
|---|---|---|
| B (control) | 197 | — |
| B + 0.01% IMIDAZOLE | 208 | 1.1 |
| B + 0.1% IMIDAZOLE | 413 | 2.1 |
| B + 1.0% IMIDAZOLE | 662 | 3.4 |

*Average of multiple determinations
**Multiple of average control determination
B — OIL/WATER EMULSION BASE Table 2 represents the consolidated results of 6 studies each study being internally controlled.

As is further evident from the data of Table 2 all imidazole derivatives tested enhanced the transdermal penetration of TPL as compared to the individual study control. Enhancement ranged from 10% to as much as 430%.

TABLE 2

2% TRIPELENNAMINE HCL IN OIL/WATER EMULSION BASE (B) WITH 0.5% IMIDAZOLE DERIVATIVES (RAT SKIN)

| COMPOSITION | 24 HOUR PENETRATION (TOTAL MICROGRAMS BASE*) | INCREASE IN PENETRATION RELATIVE TO CONTROL** |
|---|---|---|
| STUDY I | | |
| 1-METHYL IMIDAZOLE | 728 | 3.0 |
| 2-METHYL IMIDAZOLE | 615 | 2.6 |
| 1-BUTYL IMIDAZOLE | 497 | 2.1 |
| 2-HEPTADECYL IMIDAZOLE | 358 | 1.5 |
| B (CONTROL) | 239 | |
| STUDY II | | |
| 1-2 DIMETHYL IMIDAZOLE | 374 | 4.3 |
| N-TRANS-CINNAMOYL METHIMIDAZOLE | 153 | 1.8 |
| | 301 | 3.5 |
| 4-CARBOXYLIC ACID HYDRAZIDE IMIDAZOLE | 143 | 1.7 |
| B (CONTROL) | 86 | |
| STUDY III | | |
| 1-PHENYL IMIDAZOLE | 450 | 1.8 |
| 2-PHENYL IMIDAZOLE | 435 | 1.7 |
| 1-BENZYL IMIDAZOLE | 277 | 1.1 |
| 1-BENZYL-2-METHYL IMIDAZOLE | 463 | 1.8 |
| 2-PROPYL IMIDAZOLE | 554 | 2.2 |
| B (CONTROL) | 255 | — |
| STUDY IV | | |
| 1-ISOPROPYL IMIDAZOLE | 527 | 2.9 |
| N-(3-AMINOPROPYL) IMIDAZOLE | 457 | 2.5 |
| N-PROPIONYL IMIDAZOLE | 453 | 2.5 |
| 1-(3,7-DIMETHYL-2,6-OCTADIEN-1-YL) IMIDAZOLE | 479 | 2.6 |
| B (CONTROL) | 182 | — |
| STUDY V | | |
| 4-NITRO IMIDAZOLE | 142 | 1.2 |
| 1-DECYL IMIDAZOLE | 446 | 3.7 |
| 1-DODECYL IMIDAZOLE | 479 | 4.0 |
| 4-PHENYL IMIDAZOLE | 368 | 3.0 |
| 4-METHYL IMIDAZOLE | 477 | 3.9 |
| 4-(HYDROXYMETHYL)-5-METHYL IMIDAZOLE | 149 | 1.2 |
| 4-CARBOXYLIC ACID IMIDAZOLE ESTER | 252 | 2.1 |
| 1-CYANOETHYL-2-PHENYL IMIDAZOLE | 310 | 2.6 |
| B (CONTROL) | 121 | — |
| STUDY VI | | |
| 4-HYDROXYMETHYL IMIDAZOLE | 224 | 3.2 |
| D-HISTIDINE | 197 | 2.8 |
| B (CONTROL) | 70 | — |

*Average of multiple determinations
**Multiple of average control determination
B — OIL/WATER EMULSION BASE

EXAMPLE II

In order to determine the enhancement of TPL transdermal penetration by imidazole at a higher percentage of TPL, Study IV of Table 3 was carried out. As is evident from the data of Table 3 at a higher concentration of TPL (5%) with the same concentration of imidazole (0.5%), penetration of TPL was enhanced by 1190%.

EXAMPLE III

In order to ascertain the effect of the addition of isopropyl myristate (IPM, a known penetration enhancer) to a composition in accordance with the present invention, Study VII of Table 3 was carried out. The data of Table 3 demonstrate that the concentration of IPM in the composition can be reduced ten-fold while still retaining an unexpected increase in TPL penetration of 270%. This indicates that imidazole enhances the transdermal penetration effect of IPM. IPM levels sufficient to enhance transdermal penetration of pharmacologically active agents generally are irritating to skin. Use of 0.5% imidazole advantageously enables reduction to IPM concentration to 0.5% at which level IPM causes little or no skin irritation.

EXAMPLE IV (A) Study I of Table III was carried out to demonstrate the transdermal penetration enhancing effect of the imidazole derivative xylometazline HCL (XYL) on TPL.

TPL and XYL were evaluated individually in Base B as controls. Identical concentrations of TPL and XYL were then evaluated in combination. As is seen from the data of Table 3 (Study I) the composition containing the combination of TPL and XYL exhibited a 560% increase in transdermal penetration of TPL while the penetration of the imidazole derivative XYL remained fairly constant.

This demonstrates that penetration of TPL is being selectively enabled as opposed to a total breaking down of skin barrier properties.

(B) Study II was carried out in order to ascertain whether the effect observed in Study I is specified to TPL. The data of Table 3, Study II, demonstrates that the effect is not specific to TPL but additionally applies to triprologidine HCL (TRP). The combination of TRP and XYL results in a 690% increase of TRP transdermal penetration. The 90% increase in XYL transdermal penetration may be indicative of either animal variability (most likely) or a specific enhancement of XYL transdermal penetration by TRP.

(C) Study III, of Table 3, was carried out in order to determine whether a compound having the same pharmacologic activity as XYL (a vasoconstrictor) but differing in structure (viz: it is not a compound of general formula III) would enhance transdermal penetration of TRP.

The data reported in Table 3 (Study III) clearly demonstrate that the effects secured by XYL are not attributable to its vasoconstrictive properties.

EXAMPLE V

Studies V and VI of Table 3 were carried out to demonstrate that addition of imidazole to imidazole derivatives having desirable pharmacological properties (viz. naphazoline HCL (NAP) and xylometazoline HCL (XYL)) enhances the transdermal penetration of such imidazole derivatives. As shown in Table 3, (Studies V and VI), imidazole enhanced NAP and XYL penetration by 480% and 610%, respectively.

EXAMPLE V

Study VIII of Table 3 was carried out to demonstrate that yet another class of pharmacologically active compounds (antitussives e.g. dextromethophran HBR (DEX)) can have its transdermal penetration enhanced by imidazole in combination with IPM.

EXAMPLE VII

Study IX of Table 3 was carried out to demonstrate that still a further class of pharmacologically active compounds (diuretics e.g. hydrochlorothiazide (HCTZ)) can have its transdermal penetration enhanced. As is evident from the data, imidazole enhanced the transdermal penetration of HCTZ five-fold.

EXAMPLE VIII

Studies X, XI and XII of Table 3 were carried out to demonstrate that yet further classes of pharmacologically active compounds (viz. analgesics, NSAIDS and sympathomimetic amines; to wit, aspirin (ASA), ibuprofen (IBU) and metaproterenol sulfate (MET)) can have their transdermal penetration enhanced by imidazole.

TABLE 3

| IMIDAZOLE AS A PENETRATION ENHANCER (RAT SKIN) | | | |
|---|---|---|---|
| COMPOSITION | | 24 HOUR PENETRATION (TOTAL MICROGRAMS BASE*) | INCREASE IN PENETRATION RELATIVE TO CONTROL** |
| Study I | | | |
| B + 5% TPL | | 196 | — |
| B + 5% XYL | | 544 | — |
| B + 5% TPL | TPL | 1100 | 5.6 |
| + 5% XYL | XYL | 444 | 0.8 |
| Study II | | | |
| B + 5% TRP | | 180 | — |
| B + 5% XYL | | 544 | — |
| B + 5% TRP | TRP | 1250 | 6.9 |
| + 5% XYL | XYL | 1053 | 1.9 |
| Study III | | | |
| B + 5% PHE | | 266 | — |
| B + 5% TRP | | 180 | — |
| B + 5% TRP | TRP | 167 | 0.93 |
| + 5% PHE | PHE | 512 | 1.90 |
| Study IV | | | |

TABLE 3-continued

IMIDAZOLE AS A PENETRATION ENHANCER (RAT SKIN)

| COMPOSITION | 24 HOUR PENETRATION (TOTAL MICROGRAMS BASE*) | INCREASE IN PENETRATION RELATIVE TO CONTROL** |
|---|---|---|
| B + 5% TPL | 196 | — |
| B + 5% TPL + 0.5% IMI | 2336 | 11.9 |
| Study V | | |
| B + 1% NAP | 161 | — |
| B + 1% NAP + 0.5% IMI | 773 | 4.8 |
| Study VI | | |
| B + 1% XYL | 100 | — |
| B + 1% XYL + 0.5% IMI | 613 | 6.1 |
| Study VII | | |
| B + 5% TPL + 5% IPM | 104 | — |
| B + 5% TPL + 0.5% IPM + 0.5% IMI | 283 | 2.7 |
| Study VIII | | |
| B + 2% DEX | 124 | — |
| B + 2% DEX + 0.5% IPM + 0.5% IMI | 360 | 2.9 |
| Study IX | | |
| B + 5% HCTZ | 1.7 | — |
| B + 5% HCTZ + 1% IMI | 8.5 | 5.0 |
| Study X | | |
| B + 5% IBU | 181.5 | — |
| B + 5% IBU + 0.5% IMI | 378.0 | 2.1 |
| Study XI | | |
| B + 5% ASA | 87.5 | — |
| B + 5% ASA + 0.5% IMI | 370.5 | 4.2 |
| Study XII | | |
| B + 5% MET | 47.6 | — |
| B + 5% MET + 0.5% IMI | 340.5 | 7.1 |

KEY TO ABBREVIATIONS:
B — OIL/WATER EMULSION
TPL — TRIPELENNAMINE HCL
TRP — TRIPROLIDINE HCL
XYL — XYLOMETAZOLINE HCL
IMI — IMIDAZOLE
IBU — IBUPROFEN
MET — METAPROTERENOL SULFATE
NAP — NAPHAZOLINE HCL
PHE — PHENYLEPHRINE HCL
DEX — DEXTROMETHORPHAN HBR
IPM — ISOPROPYL MYRISTATE
HCTZ — HYDROCHLOROTHIAZIDE
ASA — ASPIRIN (DATA EXPRESSED AS SALICYLIC ACID)
*Average of multiple determinations
**Multiple of average control determination
B — Oil/Water Emulsion Base

EXAMPLE IX

The study of the following Table 4 was carried out to demonstrate that imidazole and its derivatives enhance transdermal penetration of still further pharmacologically active compounds through human skin. The study was carried out to demonstrate that the addition of imidazole to imidazole derivatives having desirable properties (viz. xylometazoline) enhances the transdermal penetration of such imidazole derivatives. As shown by the results of Table 4, imidazole enhanced xylometazoline penetration through human skin 5.3 fold.

TABLE 4

IMIDAZOLE AS A PENETRATION ENHANCER (HUMAN SKIN)

| COMPOSITION | 24 HOUR PENETRATION (TOTAL MICROGRAMS BASE*) | INCREASE IN PENETRATION RELATIVE TO CONTROL** |
|---|---|---|
| B + 2% XYL | 38 | — |
| B + 2% XYL + 0.5% IMI | 203 | 5.3 |

KEY TO ABBREVIATIONS:
B — OIL/WATER EMULSION
XYL — XYLOMETAZOLINE HCL
IMI — IMIDAZOLE
*Average of multiple determinations
**Multiple of average control determination

EXAMPLE X

As demonstrated earlier, imidazole (IMI) and imidazole derivatives in accordance with the present invention increase transdermal flux of pharmacologic agents. A study was conducted to determine whether increased transdermal penetration in the presence of IMI and IMI derivatives results from thermodynamic or kinetic alterations of skin transport.

Thermodynamic alterations are those resulting from increasing the solubility of the pharmacologic agent in stratum corneum (facilitating partitioning of the pharmacologic agent from the vehicle to the skin) or at the stratum corneum viable tissue interface. Kinetic alternations are those changes which act directly on the skin itself. These include reducing the diffusional barrier of the stratum corneum by changing lipid/keratin fractions or by modifying the transappendageal (sweat glands, hair follicles) route of diffusion.

To address this issue, in vitro skin penetration of tripelennamine (TPL) in 2 saturated aqueous solutions, was measured using pig skin in accordance with the Pig Skin (in vitro) procedure earlier outlined. One solution contained 0.5% IMI. The other solution served as an aqueous control (buffered with NaOH to the same pH as the IMI containing solution). The permeation data so obtained are set forth in the following Table 5.

As is evident from the data of Table 5, incorporation of IMI into the saturated TPL solution increased the skin permeation of TPL approximately 3 fold. Assuming that the stratum corneum is the rate limiting barrier for skin permeation, it is known from Fick's First Law that $P = DK$, in which:

$P$ = permeability coefficient
$D$ = diffusion coefficient of the pharmacologic agent in stratum corneum
$K$ = partition coefficient between the stratum corneum and the vehicle
$h$ = thickness of the skin Since all skin sections are dermatomed to 380 microns, h is a constant. In each composition of Table 5, the vehicle was saturated with the pharmacologic agent. Therefore, the "leaving tendency", or the thermodynamic activity of the pharmacologic agent in the vehicle, remained unchanged (K is the same for both compositions). this means that D must increase in order to explain the 3-fold increase in transdermal penetration. This is indicative of a true enhancement effect of topically applied IMI. The results of Table 5, substantiate that IMI acts as a true skin penetration enhancer. In other words, imidazole and imidazole derivatives of the present invention do not act by a thermodynamic mechanism. This may be one reason why use of a transdermal penetration enhancing amount of a selected imidazole or imidazole derivative of the present invention, in conjunction with a pharmacologically active agent whose transdermal penetration is capable of being enhanced, affords the advantageous enhancement of penetration achieved by the present invention.

TABLE 5

| | IMIDAZOLE AS A PENETRATION ENHANCER (PIG SKIN) | |
|---|---|---|
| COMPOSITION | 24 HOUR PENETRATION (TOTAL MICROGRAMS BASE*) | INCREASE IN PENETRATION RELATIVE TO CONTROL** |
| TPL/H$_2$O | 132 | — |
| TPL/H$_2$O + 0.5% IMI | 363 | 2.75 |

KEY TO ABBREVIATIONS:
TPL — TRIPELENNAMINE HCL
IMI — IMIDAZOLE
*Average of multiple determinations
**Multiple of average control determinations As is demonstrated by the data of Tables 1-5 selected imidazole and imidazole derivatives of the present invention surprisingly and unexpectedly enhance transdermal penetration of pharmacologically active compounds.

While the invention has been described with respect to various specific examples and embodiments, it is to be understood that the invention is not limited thereto and that it can be variously practiced within the scope of the following claims.

What is claimed is:

1. A topical pharmacologically active composition having enhanced transdermal penetrating activity comprising:
   (1) an effective amount of an antihistamine selected from the group consisting of: tripelennamine, tripolidine, diphenhydramine, chlorpheniramine and pharmaceutically acceptable salts thereof in combination with;
   (2) from about 0.05 wt. % to about 5.0 wt. % of a transdermal penetration enhancing agent selected from the group consisting of:
      (a) compounds of the formula

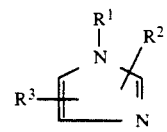

wherein R$^1$, R$^2$ and R$^3$ are independently selected from the group consisting of hydrogen, halogen, nitro, carboxylic acid hydrazide, alkyl or from 1 to 20 carbon atoms, alkoxy of from 1 to 20 carbon atoms, aryl, C$_1$-C$_5$ alkyl substituted by alkenyl of from 2 to 20 carbon atoms, amino C$_1$-C$_5$ alkyl, acyl of from 2 to 20 carbon atoms and:

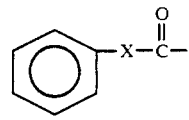

wherein X is —CH=CH— or alkylene of from 1 to 5 carbon atoms, provided that R$^2$ may also be SR$^4$ wherein R$^4$ is hydrogen or lower alkyl and provided further that at least one of R$^1$, R$^2$ and R$^3$ is hydrogen; and pharmaceutically acceptable salts thereof;
      (b) an imidazole derivative selected from the group consisting of naphazoline, xylometazoline, oxymetazoline and pharmaceutically acceptable salts thereof; and
      (c) mixtures thereof.; and
   (3) a pharmaceutically acceptable oil/water emulsion.

2. The composition according to claim 1, wherein the penetration enhancing agent is present in an amount of from about 0.25 wt. % to about 3.0 wt. %.

3. The composition according to claim 1, wherein the penetration enhancing agent is present in an amount of from about 0.5 wt. % to about 1.0 wt. %.

4. The composition according to claim 1, wherein the penetration enhancing agent is present in an amount of about 0.5 wt. %.

5. The composition according to claim 1, wherein the pharmacologically active agent is present in an amount up to about 5.0 wt. %.

6. The composition according to claim 1, further including a non skin irritating amount of isopropyl myristate.

7. The composition according to claim 1, wherein the pharmacologically active agent is tripelennamine or a pharmaceutically acceptable salt thereof.

8. The composition according to claim 7, wherein the pharmacologically active agent is tripelennamine hydrochloride.

9. The composition according to claim 8, containing 2 wt. % of tripelennamine hydrochloride and the penetration enhancing agent is imidazole.

10. The composition according to claim 9, containing from 0.1 to 1.0 wt. % imidazole.

11. A composition according to claim 9, containing 0.1 wt. % of imidazole.

12. The composition according to claim 9, containing 1.0 wt. % of imidazole.

13. The composition according to claim 1 wherein the penetration enhancing agent is selected from Group (a).

14. The composition according to claim 13 containing 2 wt. % of tripelennamine hydrochloride and wherein the penetration enhancing agent is selected from the Group consisting of:

| | |
|---|---|
| 1-methyl imidazole | 4-nitro imidazole |
| 2-methyl imidazole | 1-decyl imidazole |
| 1-butyl imidazole | 1-dodecyl imidazole |
| 2-heptadecyl imidazole | 4-phenyl imidazole |
| 1,2-dimethyl imidazole | 4-methyl imidazole |
| N-trans-cinnamoyl imidazole methimidazole | 4-(hydroxymethyl) -5 methyl imidazole |
| 4-carboxylic acid hydrazide imidazole | 4-carboxylic acid imidazole ester |
| 1-phenyl imidazole | 1-cyanoethyl-2-phenyl imidazole |
| 2-phenyl imidazole | |
| 1-benzyl imidazole | 4-hydroxymethyl imidazole |
| 1-benzyl-2-methyl imidazole | D-histidine |
| 2-propyl imidazole | |
| 1-isopropyl imidazole | |
| N-)3-aminopropyl) imidazole | |
| N-propionyl imidazole | |
| 1-(3,7-dimethyl- | |

| |
|---|
| -continued |
| 2,6-octadien-1-yl) imidazole |

15. The composition according to claim 7 containing 5 wt. % tripelennamine hydrochloride together with 0.5 wt. % imidazole.

16. The composition of claim 15 additionally containing 0.5 wt. % isopropyl myristate.

17. A topical pharmacologically active method of enhancing the transdermal penetration of an antihistamine selected from the group consisting of tripelennamine, tripolidine, diphenhydramine, chlorpheniramine and pharmaceutically acceptable salts thereof, said method comprising:

contacting an area of skin with said antihistamine and with from about 0.05 wt. % to about 5.0 wt. % of a penetration enhancing agent sufficient to enhance transdermal penetration of said active agent, said penetration enhancing agent being selected from the group consisting of:

(a) compounds of the formula:

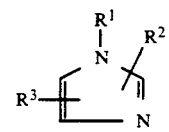

wherein $R^1$, $R^2$ and $R^3$ are independently selected from the group consisting of hydrogen, halogen, nitro, carboxylic acid hydrazide, alkyl of from 1 to 20 carbon atoms, alkoxy of from 1 to 20 carbon atoms, aryl, $C_1$–$C_5$ alkyl, acyl of from 2 to 20 carbon atoms and:

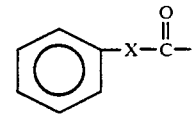

wherein X is —CH=CH— or alkylene of from 1 to 5 carbon atoms, provided that $R^2$ may also be $SR^4$ wherein $R^4$ is hydrogen or lower alkyl, and provided further that at least one of $R^1$, $R^2$ and $R^3$ is hydrogen; and pharmaceutically acceptable salts thereof;

(b) an imidazole derivative selected from the group consisting of naphazoline, xylometazoline and oxymetazoline and pharmaceutically acceptable salts thereof; and (c) mixtures thereof.

18. The composition of claim 1 containing tripelennamine.

19. The method of claim 17 wherein the antihistamine is tripelennamine.

* * * * *